(12) United States Patent
Bigg et al.

(10) Patent No.: US 6,670,400 B1
(45) Date of Patent: *Dec. 30, 2003

(54) PHENOXYETHYLAMINE DERIVATIVES HAVING HIGH AFFINITY FOR THE 5-HT$_{1A}$ RECEPTOR, PREPARATION THEREOF, USE THEREOF AS DRUGS, AND PHARMACEUTICAL COMPOSITIONS CONTAINING SAID DERIVATIVES

(75) Inventors: Dennis Bigg, Gif-sur-Yvette (FR); Jacques Pommier, Colombeš (FR); Christiane Martin, Le-Plessis-Robinson (FR); Pierre Roubert, Paris (FR); Jean Pierre Defaux, deceased, late of Rueil-Mălmaison (FR), by Christiane Charlotte Paule Defaus, Benoit Lionel Defaux, Jean-Baptiste Defaux, legal representatives

(73) Assignee: Societe de Conseils de Recherches et D'Applications Scientifiques (S.C.R.A.S.) (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/930,379
(22) PCT Filed: Apr. 5, 1996
(86) PCT No.: PCT/FR96/00518
§ 371 (c)(1),
(2), (4) Date: Apr. 8, 2002
(87) PCT Pub. No.: WO96/31461
PCT Pub. Date: Oct. 10, 1996

(30) Foreign Application Priority Data

Apr. 7, 1995 (GB) .............................. 9507288

(51) Int. Cl.$^7$ ...................... A61K 31/165; C07C 233/65
(52) U.S. Cl. .................. 514/617; 514/478; 514/507; 514/520; 514/522; 514/535; 514/598; 514/616; 514/538; 514/623; 514/624; 558/411; 558/415; 560/24; 560/27; 560/42; 560/312; 564/48; 564/50; 564/51; 564/52; 564/155; 564/185; 564/184; 564/188

(58) Field of Search ................... 564/155, 158, 564/188, 189, 184, 190, 48, 50, 51, 52; 514/616, 617, 623, 624, 598, 478, 535, 538, 520, 522, 507; 560/24, 27, 42, 312; 558/415, 411

(56) References Cited

U.S. PATENT DOCUMENTS 5,064,861 A * 11/1991 Brayer et al. ............... 514/617

FOREIGN PATENT DOCUMENTS

| EP | 0558245 | 9/1993 |
| WO | WO/9505366 | 2/1995 |

OTHER PUBLICATIONS

Patent Update, Central & Peripheral Nervous System, pps. 1233–1241 Gregory M. Shutske.
Drug Development Research, Wiley–Liss vol. 26, No. 3,1992 pp. 251–274.

* cited by examiner

Primary Examiner—Shailendra Kumar
(74) Attorney, Agent, or Firm—Muserlian, Lucas and Mercanti

(57) ABSTRACT

Phenoxyethylamine derivatives of general formula (I) having high affinity for the 5-HT$_{1A}$ receptor, methods for preparing same, pharmaceutical compositions containing said derivatives, and their use, in particular as gastric acid secretion inhibitors or as antiemetics, are disclosed. In general formula (I), Ar is phenyl substituted by one or more substituents; and R is a C$_{1-10}$ hydrocarbon radical selected from straight or branched alkyl, alkenyl or alkynyl radicals, saturated or unsaturated mono- or polycyclic cycloalkyl, cycloalkylalkyl or alkylcycloalkyl radicals; a pyridyl or isoquinolyl radical, phenyl optionally substituted by one or more substituents, and salts thereof.

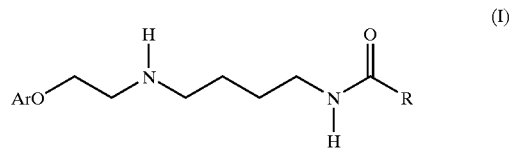

(I)

11 Claims, No Drawings

PHENOXYETHYLAMINE DERIVATIVES HAVING HIGH AFFINITY FOR THE 5-HT$_{1A}$ RECEPTOR, PREPARATION THEREOF, USE THEREOF AS DRUGS, AND PHARMACEUTICAL COMPOSITIONS CONTAINING SAID DERIVATIVES

This application is a 371 of PCT/FR96/00518, filed Apr. 5, 1996.

The neurotransmitter serotonin (5-hydroxytryptamine, 5-HT) is very important in the etiology and treatment of numerous medical problems (R. A. Glennon, *J. Med. Chem.*, 30, 1 [1987]). Many 5-HT receptors have already been identified and represent interesting objects for the selective handling of the serotoninergic function. The subtype 5-HT$_{1A}$ is especially interesting to the extent that compounds acting on this receptor may be used in the treatment of anxiety, depression, sleeping problems or cardiovascular problems (Brain 5-HT$_{1A}$ receptors: Behavioural and Neurochemical Pharmacology; Editors: C. T. Dourish, S. Ahlenius, P. H. Huston; Ellis Horwood, Ltd., Chichester [1987]). The 5-HT$_{1A}$ counteracting agents can likewise be used as anti-emetics (U. Wells, M. Ravenscroft, P. Bhandari, P. L. R. Andrews, *Med. Sci. Symp., Ser.* 5, 179 [1993]); F. Okada, Y. Torii, H. Saito, N. Matsuki, *Jpn. J. Pharmacol.*, 64,109 [1994]), or as anti-secretion agents (J. S. Gidda, J. M. Schaus, EP 455,510 A2; D. C. Evans, J. S. Gidda, *Gastroenterology*, 104, A76 [1993]).

The present invention concerns new derivatives of phenoxyethylamine having a high affinity for the 5-HT$_{1A}$ receptors, procedures for their preparation, pharmaceutical compounds comprising them, and their use especially as secretion inhibitors for gastric acid or as anti-emetics.

Object of the invention are also products of general formula I:

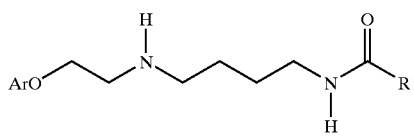

in which:
- Ar represents a phenyl substituted by one or more substitutes;
- R represents a hydrocarbonated radical containing 1 to 10 carbon atoms chosen from among the alkyl, alkenyl, linear or branched alkynyl radicals, cycloalkyl, cycloalkylalkyl or alkylcycloalkyl, monocyclic or polycyclic radicals, saturated or unsaturated;
- the pyridyl or isoquinolyl radical;
- a phenyl, which may be substituted by one or more substitutes, as well as the salts of these products.

Object of the invention is more especially products of general formula I such as defined above, characterized in that the substitute(s) which may carry the phenyl radical which represents Ar are chosen from among the halogen, lower alkyl, lower alkoxy, cyano, nitro, hydroxy, C(O)NR$^1$R$^2$, C(O)NHOR$^3$, NHC(O)R$^4$, NHC(O)NHR$^5$, CH$_2$NHC(O)NHR$^6$, CH$_2$OR, CH$_2$NHC(O)R$^8$, CO$_2$R$^9$, NHCO$_2$R$^{10}$, C(O)R$^{11}$, [and] SR$^{12}$ radicals;

in which R$^1$, R$^2$, R$^3$, R$^4$, R$^5$, R$^6$, R$^7$, R$^8$ are independently a hydrogen atom or a lower alkyl and R$^9$, R$^{10}$, R$^{11}$, R$^{12}$ are independently a lower alkyl;

and the substitute(s) which may bear the phenyl radical which may represent R are chosen from among the lower alkyl, lower alkoxy, halogen, hydroxy, nitro, amino or acylamino radicals.

In the definitions indicated above, the expression halogen represents an atom of fluorine, of chlorine, of bromine, or of iodine, preferably fluorine or iodine. The expression lower alkyl represents preferably an alkyl radical having 1 to 6 carbon atoms, linear or branched, and in particular an alkyl radical having 1 to 4 atoms of carbon such as the methyl, ethyl, propyl, isopropyl, butyl, isobutyl, secondary butyl, and tertiary butyl.

Among the alkenyl radicals, one may cite the vinyl, allyl, [and] butenyl radicals.

Among the alkynyl radicals, one may cite the ethynyl or propargyl radicals. Among the acylamino radicals, one may cite the acetylamino [and] propionylamino radicals.

The lower alkoxy radicals may correspond to the alkyl radicals indicated above. The methoxy, ethoxy, or isopropyloxy radicals are preferred.

The saturated monocyclic cycloalkyls may be chosen from among the radicals having 3 to 7 carbon atoms such as the cyclopropyl, cyclobutyl, cyclopentyl, cyclohexyl, or cycloheptyl radicals.

The mono- or polysaturated cycloalkyl radicals may be chosen from among the cyclobutene, cyclopentene, cyclohexene, cyclopentanediene, cyclohexadiene.

Examples of the polycyclic cycloalkyl radical are bicyclo-[2,2,1]-heptyl or adamantyl.

The products of formula I may form addition salts with the acids, especially pharmacologically acceptable acids.

Examples of salts are given below in the experimental part.

A particular object of the invention is general formula I compounds such as are described above, characterized in that Ar represents a phenyl radical substituted by a substitute chosen from among the hydroxy, methoxy, —C(O)NHMe, —NHC(O)Me, —NHCO$_2$R'$_{10}$, with R'$_{10}$ representing a methyl or ethyl radical, —NHCONH$_2$, —C(O)NHOH and R represents a cyclopentyl, cyclohexyl, cycloheptyl, cyclopentylmethyl, adamantyl, tertiary butyl, neopentyl, phenyl, [or] fluorophenyl radical.

The substitutes of the phenyl radical which may represent Ar are preferably situated in position 2 or 3.

More especially, the object of the invention are products described below in the examples, especially products responding to the following formulas:

N[4-{2-(2-methoxyphenoxy)ethyl}aminobutyl] benzamide;

N[4-{2-(2-methoxyphenoxy)ethyl}aminobutyl] adamantamide;

N[4-{2-(2-methylamino carbonyl phenoxy)ethyl] amino}butyl]benzamide;

N[4-{2-(2- hydroxyphenoxy)ethyl}aminobutyl] benzamide;

N[4-{2-(2- methoxyphenoxy)ethyl}aminobutyl] cyclohexylamide;

N[4-{2-(2- methoxyphenoxy)ethyl}aminobutyl] cycloheptylamide;

N[4-{2-(2- methoxyphenoxy)ethyl}aminobutyl]2-bicyclo [2,2,1]heptylamide;

as well as the salts of these compounds with organic or mineral acids.

The object of the invention is likewise a preparation procedure for general formula I products as defined above, characterized in that:

A) Either it is a formula II product:

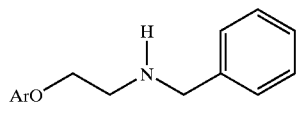

II in which Ar has the meaning indicated above, with a product of formula III:

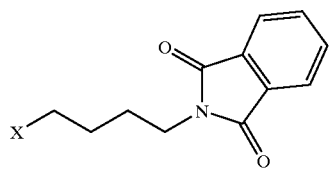

III in which X represents a halogen or a pseudo-halogen to obtain a product of formula IV:

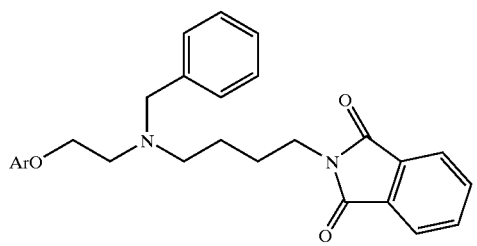

IV which formula IV product is subjected to a reaction for eliminating the phthalimide group to obtain a formula V product:

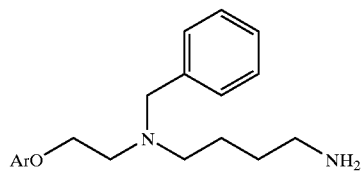

V which formula V product is treated by an acylation reagent derived from RCO$_2$H acid in which R has the meaning indicated above to obtain a product of formula VI:

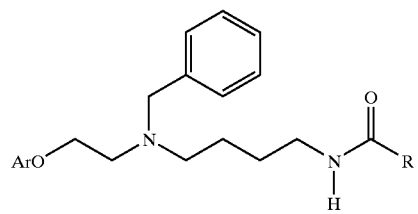

VI

B) or one causes a reaction of a product of formula VII:

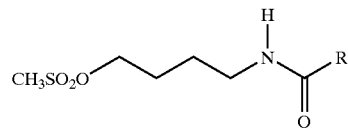

VII with N-benzylethanolamine of formula:

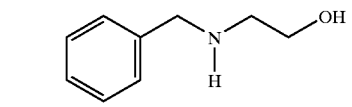

to obtain a product of formula VIII:

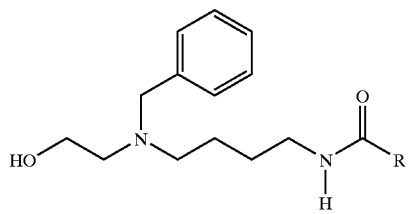

VIII which is converted into a product of formula IX:

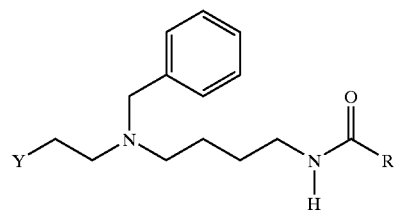

IX in which Y represents a halogen or pseudo-halogen radical, a product of formula IX which is converted into a product of formula VI as previously defined, by causing a reaction of a phenol derivative of formula ArOH and formula VI products, which is converted into a product of formula I by splitting the benzyl function and formula I products which is converted, if desired, into acid salts by the action of the corresponding acid.

Reaction Diagram 1

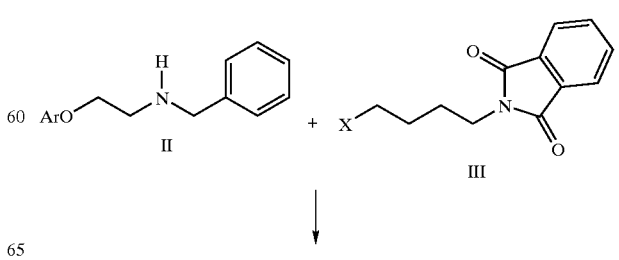

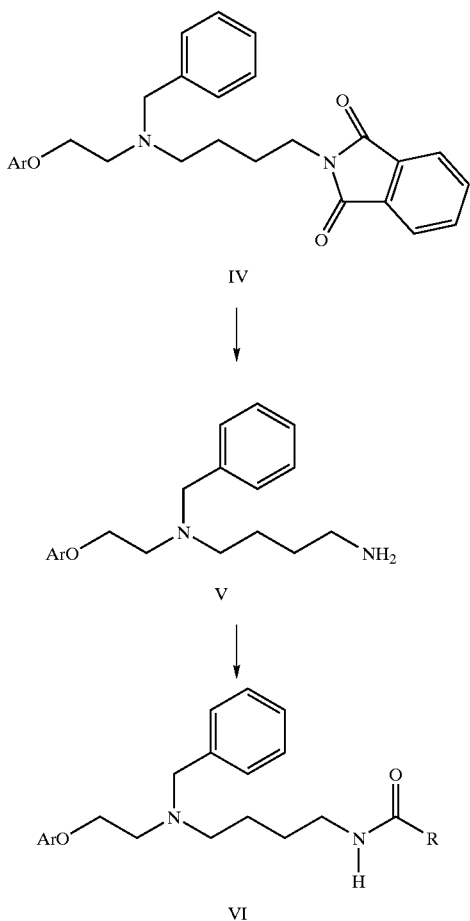

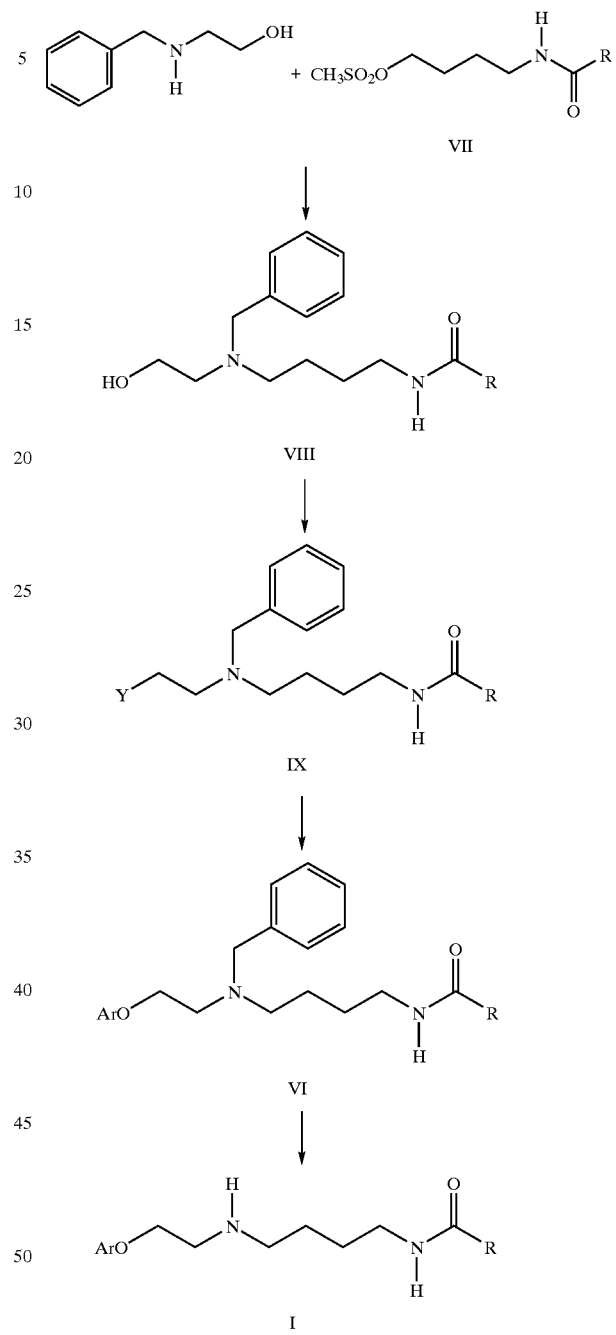

In this reaction diagram, Ar and R are as defined above and X represents a starting group such as chloro, bromo, iodo, methanesulphonyloxy, benzenesulphonyloxy, or p-toluenesulphonyloxy, in other words, a halogen or pseudo halogen group.

The reaction of a compound of general formula II with a compound of general formula III to obtain a compound of general formula IV can be readily accomplished by heating in a polar solvent, for example, acetonitrile or dimethylformamide in the presence of an acid acceptor such as potassium carbonate or sodium carbonate. Phthalimides of general formula IV may be converted into primary amines of general formula V according to conventional methods, for example by heating with hydrazine hydrate, preferably in a solvent such as ethanol. The primary amines of general formula V thus obtained may be converted into amides of general formula VI by reaction with a derivative of the acid $RCO_2H$ which may be the appropriate acid chloride or the acid anhydride or other activated acid derivatives such as those generally used in peptide coupling reactions. The reaction is carried out in an inert solvent such as ether, tetrahydrofurane, or dichloromethane and generally in the presence of an acid acceptor such as a tertiary amine, for example, triethylamine or di-isopropylethylamine.

In this reaction diagram Ar and R are as defined above and Y, identical to or different from X, represents a starting group such as chloro, bromo, iodo, methanesulphonyloxy, benzenesulphonyloxy, or p-toluenesulphonyloxy, in other words, a halogen or pseudo-halogen group.

Compounds of general formula VIII may be prepared by heating a compound of general formula VII with N-benzylethanolamine in a polar solvent such as an alcohol, in the presence of an acid acceptor such as a tertiary amine or an inorganic base such as sodium carbonate or potassium carbonate. Alternatively, compounds of general formula VIII can be readily prepared simply by heating a compound of general formula VII with an excess of N-benzylethanolamine in the absence of a solvent, preferably in a nitrogen atmosphere and to a temperature ranging between 60 degrees C. and 90 degrees C.

Compounds of general formula VIII thus obtained may be converted for example into chlorides of general formula IX (Y=Cl) by reaction with a chloride of methanesulphonyl in an inert solvent such as dichloromethane in the presence of an organic base such as triethylamine or di-isopropylethylamine. Compounds of general formula VI may be prepared from compounds of general formula IX by allowing the latter to react with a phenoxide anion produced from the appropriate ArOH phenol by using a base such as sodium hydroxide, potassium hydroxide, or sodium hydride. The reaction is carried out in an aprotic solvent and preferably in a dipolar aprotic solvent, for example dimethylformamide.

General formula I compounds are obtained by de-protecting the compounds of general formula VI according to known general methods for debenzylation, for example, catalytic hydrogenation or reaction with a choroformate such as vinyl chloroformate or α-chloroethyl chloroformate followed by hydrolysis or methanolysis. Other methods of debenzylation such as described in "Protective Groups in Organic Synthesis" (T. W. Green, P. G. M. Wuts; 2nd edition, J. Wiley and Sons, Inc., pp. 364–66 [1991]) may likewise be used to the extent that they are compatible with the substitutes with the aryl core(s) of the compounds of general formula VI.

Any salification of formula I products is likewise carried out according to the usual methods indicated below in the experimental part.

The compounds of the present invention have interesting pharmacological properties. It is thus that one has discovered that the compounds of the present invention have a high affinity for the $5HT_{1A}$ receptor.

The compounds of the present invention may thus be used in various therapeutic applications.

The compounds may inhibit gastric acid secretion and induced vomiting, for example, by cis-platinum. Thus, the compounds of the invention may be used as anti-emetics or for the treatment of illnesses in which it is necessary or desirable to reduce gastric acid secretion, for example, gastric or duodenal ulcers, [or] gastritis, gastroesophagial reflux, gastric dyspepsia, Zollinger-Ellison's syndrome, [or] nausea.

The compounds of the invention likewise exert an effect on gastric emptying and intestinal motility. For example, they may be used to fight against constipation, post-surgical atony, [or] gastroparesia.

They may likewise be used to fight against certain diseases of the nervous system such as anxiety, depression, sleep problems such as insomnia, dependence upon certain drugs, Alzheimer's disease, eating disorders such as anorexia, [or] dizziness. The compounds of the invention may likewise be used to treat diseases of the cardiovascular system, especially hypertension.

There is below in the experimental part an illustration of the pharmacological properties of the compounds of the invention.

These properties make the formula I products suitable for a pharmaceutical use. The present application likewise has as its object, by way of medications, the formula I products as defined above as well as addition salts with pharmaceutically acceptable organic or mineral acids of said formula I products, as well as pharmaceutical compounds comprising as the active principle, at least one of the medications as defined above.

The invention concerns as well pharmaceutical compounds containing a compound of the invention or a pharmaceutically acceptable acid addition salt of the latter, in association with a pharmaceutically acceptable vehicle. The pharmaceutical compound may be in the form of a solid, for example powders, granules, tablets, gels, or suppositories. The appropriate solid vehicles may be for example calcium phosphate, magnesium stearate, talc, sugars, lactose, dextrin, starch, gelatin, cellulose, methyl cellulose, sodium carboxymethyl cellulose, polyvinyl pyrrolidine, and wax.

Pharmaceutical compounds containing a compound of the invention may also be present in liquid form, for example, solutions emulsions, . . . suspensions or syrups. Appropriate liquid vehicles may be for example water, organic solvents such as glycerol or glycols as well as their mixtures in water in various proportions, added to oils or pharmaceutically acceptable fats. Sterile liquid compounds may be used for intramuscular, intraperitoneal, or subcutaneous injections, and sterile compounds may likewise be administered intravenously.

The invention likewise has as its object the use of formula I products as defined above for the preparation of antiemetic medications, medications intended to reduce gastric secretion, medications intended to accelerate gastric emptying, medications intended to accelerate the intestinal transit, medications intended to treat anxiety, depression, [or] sleep problems, as well as medications intended to treat cardiovascular diseases.

The invention likewise has as its object by way of new industrial products and especially by way of new industrial products intended for the preparation of formula I products, the products of formulas IV, V, VI, VIII, and IX as described above.

The starting products of the invention, especially the products of formulas II, III, and VII, are known products or those which may be prepared from known products. One may cite the following references: N-benzylethanolamine is a product marketed for example by the company ACROS.

The formula II products may be prepared by classical methods from the corresponding phenoxy ethyl amines, for example by the intermediary of benzamide followed by a reduction by lithium aluminum hydride or an equivalent method. Alternatively, one may use a reducing amination according to the usual methods.

Phenoxyethylethylamines may be prepared according to the usual methods, for example by reaction of a phenol with chloracetonitrile in a basic medium, [which] reaction [is] followed by the reduction of the nitrile by lithium aluminum hydride according to the method described in Chim. Ther. 8 (3) 259–270 (1973).

Formula III products are commercially [available] or may be manufactured by methods known to the person skilled in the art.

Thus it is that the product of formula III in which X represents a bromine atom is marketed by the company ACROS.

The products of formula III in which X represents another halogen atom such as chlorine or iodine or a pseudo-halogen such as the mesyl, tosyl, [or] phylsulfonyl radicals may be prepared by the usual methods from the corresponding alcohol marketed by the company Maybridge.

The products of formula VII may be prepared from omega—hydroxybutyl amide according to known methods for the formation of a mesylate from an alcohol, for example according to the method described in J. Org. Chem. 35(9), 3195–6 (1970).

The following examples are presented to illustrate the procedures above and must not in any case be considered as limiting the scope of the invention.

EXPERIMENTAL PART

EXAMPLE 1

N-[4-{2-(2-Methoxyphenoxy)ethyl}aminobutyl]
benzamide (I, Ar=2-Methoxyphenyl. R=Phenyl:
Compound No. 1, Table 1)

First Stage

N-[4-Benzyl[2-(2-methoxyphenoxy)ethyl]
aminobutyl]phthalimide (IV, Ar=2-Methoxyphenyl)

A solution of N-[4-bromobutyl] phthalimide (9.87 g, 0.035 mole) in acetonitrile (200 ml) is added to a hot solution (60 degrees C.) of N-benzyl [2-(2-methoxy phenoxy]ethylamine (8.5 g, 0.033 mole) in acetonitrile (170 ml) comprising potassium carbonate (9.1 g, 0.066 mole). The mixture is stirred and heated to reflux for 6 hours, then left to cool to ambient temperature, filtered, and the solvent is evaporated at reduced pressure. The residue is recovered in dichloromethane (500 ml), washed with water (3×50 ml) and dried over magnesium sulfate. The filtration and evaporation of the solvent yield an oil which is purified by flash chromatography on silica gel using ethyl acetate/heptane (1/4,then 3/7) as eluant in order to obtain 7.2 g (48%) of compound IV in the form of an oil.

NMR (CDCl$_3$), δ: 1.5–1.7 (m, 4H), 2.54–2.67 (t, 2H), 2.84–2.97 (t, 2H), 3,59–3.73 (m, 4H), 3.83 (s, 3H), 3.99–4.15 (m, 2H), 6.79–6.89 (m, 4H), 7.20–7.32 (m, 5H), 7.64–7.88 (m, 4H).

Second Stage

N-Benzyl-N-[2-(2-methoxyphenoxy)ethyl]-1,4-
butanediamine (V, Ar=2-Methoxyphenyl)

A solution of hydrazine hydrate solution (0.83 ml, 0.017 mole) in ethanol (20 ml) is added to a solution of N-[4-{benzyl[2-(2-methoxyphenoxy)ethyl]amino}butyl] phthalimide (7.2 g, 0.016 mole) in ethanol (70 ml), the solution is stirred and heated to reflux for 3 hours. After cooling to ambient temperature, the solvent is evaporated at reduced pressure and the residual oil is treated with 1 N hydrochloric acid (40 ml). The precipitate formed is removed by filtration, washed in water, and the filtrate and the washing liquids are made basic with potassium carbonate (16 g). The separated oil is extracted with dichloromethane (3×80 ml) and the extracts dried over magnesium sulfate. Filtration and evaporation of the solvent at reduced pressure yields 4.4 g (86%) of the theoretical yield in the form of an oil. The treatment of an etherized solution of the free base with a saturated solution of hydrogen chloride gas in ether makes it possible to obtain N-benzyl-N-[2-(2-methoxyphenoxy)ethyl]-1,4-butanediamine as a dihydrochlorated salt; mp 200–202 degrees C. after recrystallization from ethanol.

Third Stage

N-[4-{Benzyl[2-(2-methoxyphenoxy)ethyl]amino)
butyl]benzamide (VI, Ar=2-Methoxyphenyl, R=
Phenyl)

While stirring and cooling (5–10 degrees C.), a solution of benzoyl chloride (0.9 ml, 0.0076 mole) in tetrahydrofurane (25 ml) is added to a solution of triethylamine (1.05 ml, 0.0076 mole) in tetrahydrofurane (25 ml). After 30 minutes at 10 degrees C., followed by 1.5 hours at ambient temperature, the solvent is evaporated at reduced pressure. The residue is recovered in dichloromethane; the solution is washed with water and dried over magnesium sulfate. Filtration and evaporation of the solvent at reduced pressure yield an oil which is purified by flash chromatography over silica gel by using ethyl acetate/hexane (1/1, then 3/2) as eluant to obtain 2 g (61%) of the theoretical in the form of an oil.

NMR (CDCl$_3$), δ: 1.58–1.85 (m, 4H), 2.60–2.66 (m, 2H), 2.85–2.97 (t, 2H), 3.39–3.45 (m, 2H). 3.66 (s, 2H), 3.8 (s, 3H), 3.99–4.12 (t, 2H), 6.42 (large s, 1H), 6.76–6.90 (m, 4H), 7.21–7.46 (m, 8H), 7.66–7.77 (m, 2H).

Fourth Stage

N-[4{2-(2-Methoxyphenoxy)ethyl}aminobutyl]
benzamide (I, Ar=2-Methoxyphenyl, R=Phenyl:
Compound No. 1, Table 1)

A catalyst comprising palladium on carbon (0.8 g of 10%) is added to a solution of N-[4-{benzyl[2-(2-methoxyphenoxy)ethyl]amino}butyl]benzamide (2 g, 0.0046 mole) in methanol (30 ml) and the mixture is hydrogenated at 1.5 psi at ambient temperature. When the hydrogen absorption is completed (around three hours) the catalyst is removed by filtration and the solvent is evaporated at reduced pressure to obtain 1.2 g (76%) of compound I in the form of oil. The treatment of an etherized solution of the free base with a saturated solution of gaseous hydrochloric acid in ether yields 1.0 g (59%) of dihydrochlorate of compound No. 1 in the form of white crystals, mp 118–120 degrees C.

EXAMPLE 2

N-[4-{-2-(2-Methoxyphenoxy)ethyl}aminobutyl]-1-
adamantamide (I, Ar=2-Methoxyphenyl, R=1-
Adamantyl: Compound No. 2, Table 1)

First Stage

N-[4-{Benzyl[2-(2-methoxyphenoxy)ethyl]
amino}butyl]-1-adamantamide (VI, Ar=2-
Methoxyphenyl, R=1-Adamantyl)

The chloride of 1-adamantylcarbonyl (2.14 g, 0.011 mole), by portions, in a cooled solution (five degrees C.) of N-benzyl-N-[2-(2- methoxyphenoxy)ethyl]-1,4-butanediamine (3.28 g, 0.01 mole) prepared according to the method described in Example 1, and triethylamine (1.54 ml, 0.011 mole) in tetrahydrofurane (40 ml) are added. After 30 minutes the reaction mixture is reheated to ambient temperature and one hour later the solvent is evaporated at reduced pressure. The residue is recovered in dichloromethane, washed in water, and dried over magnesium sulfate. The filtration and evaporation of the solvent at reduced pressure yield an oil which is purified by flash chromatography over silica gel by using ethyl acetate/hexane (1/2 then 3/4) as eluant to obtain 3 g (61%) of the compound expected in the form of an oil.

NMR (CDCl$_3$), δ: 1.24–1.29 (m, 2H), 1.53–1.67 (m, 4H), 1.67–1.94 (m, 14H), 2.5–2.7 (m, 2H), 2.93–2.96 (t, 2H), 3.21–3.23 (m, 2H), 3.71 (s, 2H), 3.85 (s, 3H), 4.07–4.10 (t, 2H), 6.82–6.92 (m, 4H), 7.24–7.37 (m, 5H).

Second Stage

N-[4-{2-(2-Methoxyphenoxy)ethyl}aminobutyl]-1-
Adamantamide (I, Ar=2-Methoxyphenoxy, R=1-
Adamantyl: Compound No. 2, Table 1)

1.5 g of a catalyst comprised of palladium on carbon at 10% are added to a solution of N-[4-{benzyl[2-(2- methoxyphenoxy)ethyl]amino}butyl]-1-adamantamide (2.85 g, 0.058 mole) in methanol (30 ml) and the mixture is hydrogenated at 1.5 psi at ambient temperature. When the hydrogen absorption is terminated (around three hours) the catalyst is removed by filtration and the solvent evaporated at reduced pressure to yield 2 g (87%) of compound I in the form of oil. The treatment of a solution of this free base (0.6 g) in acetone with a solution of fumaric acid (0.17 g) in acetone produces 0.5 g of the fumarate of compound No. 2 in the form of white crystals, mp 122–124 degrees C.

EXAMPLE 3

N-[4-{2-(2-Nitrophenoxy)ethyl]amino}butyl] benzamide (I, Ar=2-Nitrophenyl, R=Phenyl: Compound No. 8, Table 1)

First Stage

N-[4-{Benzyl (2-hydroxyethyl)amino}butyl] benzamide (VIII, R=Phenyl)

A mixture of N-benzylamino ethanol (60.5 g, 56.8 ml, 0.4 mole) and N-[4-(methanesulphonyloxy) butyl]benzamide (51.5 g, 0.19 mole) is heated for two hours at 75–80 degrees C. in a nitrogen atmosphere. The reaction mixture is cooled, recovered in dichloromethane (400 ml), the solution is washed in water (3×100 ml), then dried over magnesium sulfate. The solution is filtered and the solvent is removed at reduced pressure to obtain an oil which crystalizes with di-isopropyl ether in order to obtain 51.5 g (83%) of compound VIII in the form of white crystals, mp 61–62 degrees C.

Second Stage

N-[4-{Benzyl (2-chloroethyl)amino}butyl] benzamide (IX, R=Phenyl, Y=Cl)

Methanesulphonyl chloride (14.8 g, 10 ml, 0.13 mole) is added dropwise while stirring, to a cooled solution (5 degrees C.) of N-4{benzyl (2-hydroxyethyl)amino}butyl] benzamide (35 g, 0.11 mole) in dichloromethane (300 ml). The solution is brought to ambient temperature and after 1.5 hour triethylamine (13 g, 18 ml, 0.13 mole) is added and the stirring is continued for another 1.5 hours. The reaction mixture is washed in ice water (150 ml), in water saturated with salt (2×100 ml) and dried over magnesium sulfate. Filtration and evaporation of the solvent at reduced pressure yield 36.6 g (99%) of the compound expected in the form of a light brown oil which crystalizes when kept at 4 degrees C.

NMR (CDCl$_3$), δ: 1.58–1.67 (m, 4H), 2.58 (m, 2H), 2.83 (t, 2H, J=6.8 Hz), 3.40–3.45 (q, 2H, J=6.5 Hz), 3.51 (t, 2H, J=6.8 Hz), 3.66 (s, 2H), 6.19 (s, 1H), 7.24–7.48 (m, 8H), 7.73–7.75 (m, 2H).

Third Stage

N-[4-{Benzyl[2-(2-nitrophenoxy)ethyl]amino}butyl] benzamide (VI, Ar=2-Nitrophenyl, R=Phenyl)

2-nitrophenol (0.56 g, 0.004 mole) is added in portions to a stirred suspension of sodium hydride (160 mg of a dispersion at 60% in oil, 0.004 mole) in dry dimethylformamide (10 ml) in a nitrogen atmosphere. When the hydrogen evolution is completed, while stirring, a solution of N-[4-{benzyl (2-chloroethyl)amino}butyl]benzamide (1.6 g, 0.0046 mole) in dry dimethylformamide (5 ml) is added dropwise. The reaction mixture is heated to 65–70 degrees C. for 1.5 hours, cooled back to ambient temperature, and poured over crushed ice. The mixture is extracted with ether (50 ml); the organic phase is separated and washed with water (3×20 ml) before being dried over magnesium sulfate. Filtration and evaporation of the solvent at reduced pressure yield 1.3 g of an oil which is purified by flash chromatography over silica gel by using a mixture of ethyl acetate/heptane (3/1) as eluant. The expected compound is obtained in the form of oil (0.94 g, 52%).

NMR (CDCl$_3$), δ: 1.59–1.65 (m, 4H), 2.62 (t, 2H, J=0.65 Hz), 2.92 (t, 2H, J=0.55 Hz), 3.42–3.45 (m, 2H), 3.67 (s, 2H), 4.09 (t, 2H, J=0.55 Hz), 6.45 (s, 1H), 6.95–6.98 (m, 2H), 7.20–7.32 (m, 5H), 7.38–7.46 (m, 4H), 7.76–7.79 (m, 3H).

Fourth Stage

N-[4-{2-(2-Nitrophenoxy)ethyl)amino}butyl] benzamide (I, Ar=2-Nitrophenyl, R=Phenyl: Compound No. 8, Table 1)

A solution of α-chloroethylchloroformate (0.28 g, 0.002 mole) in dry dichloroethane (1.8 ml) is added dropwise to a solution of N-[4-{benzyl[2-(2-nitroxyphenoxy)ethyl] amino}butyl]benzamide (0.82 g, 0.18 mole) in dry dichloroethane (9 ml) in a nitrogen atmosphere and while cooling in an ice bath. At the end of two hours, the solvent is evaporated at reduced pressure; the residue is recovered in methanol (10 ml) and heated for one hour to reflux. The solvent is concentrated at reduced pressure and ethyl acetate (10 ml) is added. The precipitate formed is collected by filtration, washed with ethyl acetate [and] diethyl ether and dried to obtain 0.55 g (76%) of compound I in the form of hydrochlorate, mp 159.5–160 degrees C.

EXAMPLE 4

N-[4-{2-(2-Methylaminocarbonylphenoxy)ethyl] amino}butyl]benzamide (I, Ar=2-MeNHC(O)C$_6$H$_4$, R=Phenyl: Compound No. 18, Table 1)

First Stage

N-[4-{Benzyl[2-(2-methylaminocarbonylphenoxy) ethyl]amino}butyl]benzamide (VI, Ar=2-MeNHC (O)C$_6$H$_4$, R=Phenyl)

A solution of N-{4-[benzyl (2-chloroethyl)amino}butyl] benzamide (8.1 g, 0.023 mole) prepared according to the method described in Example 3 in dimethyl formamide (50 ml) is added to a stirred solution of sodium 2-methylaminocarbonyl-phenoxide prepared in situ from 2-methylaminocarbonylphenol (3.0 g, 0.02 mole), sodium hydroxide (0.8 g, 0.02 mole) and water (4 ml) in dimethylformamide (50 ml). The mixture is heated to 85 degrees C. for 4 hours, cooled to ambient temperature, and poured into a mixture of ice and water. The mixture is extracted with ethyl acetate (250 ml) and the organic phase is washed with 2% aqueous sodium hydroxide (100 ml), salt water (3×50 ml) and dried over magnesium sulfate. Filtration and evaporation of the solvent at reduced pressure yield a yellow oil which is purified by flash chromatography over silica gel by using ethyl acetate as eluant in order to obtain 5.2 g (57%) of compound VI in the form of oil.

NMR (CDCl$_3$), δ: 1.35–1.80 (m, 4H), 2.40–2.65 (m, 2H), 2.84–2.94 (m, 4H), 3.34–3.44 (m, 2H), 3.65 (s, 2H), 4.16 (t, 2H, J=5.5 Hz), 6.30–6.65 (m, 1H), 6.84–7.09 (m, 2H), 7.26–7.48 (m, 8H), 7.72–7.82 (m, 2H), 8.13–8.23 (m, 2H).

Second Stage

N-[4-{2-(2-Metholaminocarbonylphenoxy)ethyl]amino}butyl]benzamide [sic](I, Ar=2-MeNHC(O)C$_6$H$_4$, R=Phenyl: Compound No. 18, Table 1)

A catalyst comprising palladium over carbon at 10%, water deactivated, is added to a solution of N-[4-{benzyl[2-(2-methylaminocarbonylphenoxy)ethyl]amino}butyl]benzamide (6.6 g, 0.015 mole) in methanol (200 ml) and the mixture is hydrogenated at atmospheric pressure and ambient temperature. When the absorption of hydrogen is completed (around three hours), the catalyst is eliminated by filtration and the filtrate evaporated at reduced pressure. The residue is collected in acetone (15 ml) and treated with a fumaric acid solution (1.04 g, 0.009 mole) in acetone (100 ml). The oily solid which separates by precipitation is crystalized with the addition of isopropanol (50 ml). The white crystalline product is collected by filtration, washed with acetone, and dried to obtain 2.7 g (38%) of compound No. 18 in the form of hemifumarate, mp 159–161 degrees C.

The procedures described above yield a compound of the invention in the form of a free base or an addition salt with an acid. If the invention compound is obtained in the form of an addition salt with an acid; the free base may be obtained by basifying an addition salt solution with an acid. Conversely, if the product of the procedure is a free base, the addition salt with an acid, in particular an addition salt with a pharmaceutically acceptable acid, may be obtained by dissolving the free base in an appropriate organic solvent and by treating the solution with an acid according to conventional procedures of preparing addition salts with an acid from free bases.

Examples of addition salts with an acid are those derived from inorganic acids such as sulfuric, hydrochloric, hydrobromic, or phosphoric acid, or organic acids such as tartaric, fumaric, maleic, citric, caprylic, oxalic, benzoic, methanesulphonic, p-toluenesulphonic, benzenesulphonic, succinic, or acetic acid.

For compounds of the invention containing an asymetric center, racemic mixtures and individual optically active isomers are likewise considered as being within the scope of the invention.

Table 1 below shows the main compounds prepared according to the above procedures and which illustrate the invention without limiting its scope. Compounds No. 1, 2, 8, and 18 correspond to the products of examples 1, 2, 3, and 4 described above. The other products may be prepared by using the same procedure.

TABLE 1

| Compound No. | Ar | R | Salt | mp (degrees C.) |
|---|---|---|---|---|
| 1 | 2-MeO.C$_6$H$_4$ | C$_6$H$_5$ | hydrochlorate | 118–120 |
| 2 | 2-MeO.C$_6$H$_4$ | 1-adamantyl | fumarate | 122–124 |
| 3 | 2-MeO.C$_6$H$_4$ | 2-pyridyl | dihydrochlorate | 152–154 |
| 4 | 2-MeO.C$_6$H$_4$ | 2-isoquinolyl | dihydrochlorate | 166–168 |
| 5 | 2-$^i$PrO.C$_6$H$_4$ | C$_6$H$_5$ | hydrochlorate | 108–110 |
| 6 | 2-H$_2$NC(O).C$_6$H$_4$ | C$_6$H$_5$ | hydrochlorate | 128–132 |
| 7 | 2-MeO.C$_6$H$_4$ | 2-MeC(O)NH.C$_6$H$_4$ | hydrochlorate | 92–94 |
| 8 | 2-O$_2$N.C$_6$H$_4$ | C$_6$H$_5$ | hydrochlorate | 159.5–160 |
| 9 | 2-NC.C$_6$H$_4$ | C$_6$H$_5$ | hydrochlorate | 168–168.5 |
| 10 | 2-HOCH$_2$.C$_6$H$_4$ | C$_6$H$_5$ | hydrochlorate | 144–145.5 |
| 11 | 2-MeS.C$_6$H$_4$ | C$_6$H$_5$ | hydrochlorate | 140–140.5 |
| 12 | 2-MeO.C$_6$H$_4$ | 2-HO.C$_6$H$_4$ | hemifumarate | 140–142 |
| 13 | 2-MeO.C$_6$H$_4$ | 2-MeO.C$_6$H$_4$ | fumarate | 120–122 |
| 14 | 2-MeO.C$_6$H$_4$ | 3-MeO.C$_6$H$_4$ | fumarate | 68–70 |
| 15 | 2-MeO.C$_6$H$_4$ | 4-MeCH(OH).C$_6$H$_4$ | hemifumarate | 152–154 |
| 16 | 2-MeC(O).C$_6$H$_4$ | C$_6$H$_5$ | hydrochlorate | 187–192.5 |
| 17 | 2-MeO.C$_6$H$_4$ | 2-MeO.C$_6$H$_4$ | hemifumarate | 135–137 |
| 18 | 2-MeNHC(O).C$_6$H$_4$ | C$_6$H$_5$ | hemifumarate | 159–161 |
| 19 | 3-H$_2$NC(O).C$_6$H$_4$ | C$_6$H$_5$ | hydrochlorate | 264–266.5 |
| 20 | 2-HO.C$_6$H$_4$ | C$_6$H$_5$ | hydrochlorate | 252–254.5 |
| 21 | 2-MeC(O)NH.C$_6$H$_4$ | C$_6$H$_5$ | free base | 74–78 |
| 22 | 2-MeO.C$_6$H$_4$ | 4-O$_2$N.C$_6$H$_4$ | hydrochlorate | 162.5–163.5 |
| 23 | 2-MeO.C$_6$H$_4$ | 4-F.C$_6$H$_4$ | hydrochlorate | 119–120.5 |
| 24 | 2-F.C$_6$H$_4$ | C$_6$H$_5$ | hydrochlorate | 167–168 |
| 25 | 3-MeO.C$_6$H$_4$ | C$_6$H$_5$ | hydrochlorate | 174–175.5 |
| 26 | 2-MeO.C$_6$H$_4$ | $^t$butyl | fumarate | 149–151 |
| 27 | 2-Me.C$_6$H$_4$ | C$_6$H$_5$ | hydrochlorate | 162–163 |
| 28 | 2,3-(MeO)$_2$.C$_6$H$_3$ | C$_6$H$_5$ | hydrochlorate | 141.5–142 |
| 29 | 2-MeO.C$_6$H$_4$ | 2,6-Me$_2$.C$_6$H$_3$ | fumarate | 123–125 |
| 30 | 2-MeO.C$_6$H$_4$ | 3-I.C$_6$H$_4$ | hydrochlorate | 121–121.5 |
| 31 | 3-MeNHC(O).C$_6$H$_4$ | C$_6$H$_5$ | hydrochlorate | 227–229 |
| 32 | 2-Me$_2$NC(O).C$_6$H$_4$ | C$_6$H$_5$ | fumarate | 126–128.5 |
| 33 | 2-MeO.C$_6$H$_4$ | CH$_2$$^t$Bu | fumarate | 130–132 |
| 34 | 2-MeO.C$_6$H$_4$ | cyclohexyl | fumarate | 134–136 |
| 35 | 2-MeO.C$_6$H$_4$ | isopropyl | fumarate | 120–122 |
| 36 | 2-HONH(CO).C$_6$H$_4$ | C$_6$H$_5$ | oxalate | 147–148.5 |
| 37 | 2,6-(MeO)$_2$.C$_6$H$_3$ | C$_6$H$_5$ | oxalate | 166–167.5 |
| 38 | 3-H$_2$NC(O)NH.C$_6$H$_4$ | C$_6$H$_5$ | hydrochlorate | 193–194 |
| 39 | 2-MeO.C$_6$H$_4$ | (CH$_2$)$_4$Me | fumarate | 110–112 |
| 40 | 2-MeNHC(O)NHCH$_2$.C$_6$H$_4$ | C$_6$H$_5$ | oxalate | 170–171.5 |
| 41 | 2-MeO.C$_6$H$_4$ | CH($^n$Pr)$_2$ | fumarate | 118–120 |
| 42 | 2-MeO.C$_6$H$_4$ | CH$_2$CH(Me)$_2$ | fumarate | 134–136 |
| 43 | 2-MeO.C$_6$H$_4$ | cyclopentyl | fumarate | 122–124 |
| 44 | 2-MeO$_2$C.C$_6$H$_4$ | C$_6$H$_5$ | hydrochlorate | 103–106 |
| 45 | 2-MeO.C$_6$H$_4$ | 1-methylcyclohexyl | fumarate | 120–122 |

TABLE 1-continued

| Compound No. | Ar | R | Salt | mp (degrees C.) |
|---|---|---|---|---|
| 46 | 2-MeO.$C_6H_3$ | cycloheptyl | fumarate | 125–126 |
| 47 | 2-MeNHC(O).$C_6H_4$ | $CH_2{}^tBu$ | hemifumarate | 137–138 |
| 48 | 3-MeNHC(O).$C_6H_4$ | $^tBu$ | hydrochlorate | 169–171.5 |
| 49 | 3-MeC(O)NH.$C_6H_4$ | $^tBu$ | hydrochlorate | 164–165.5 |
| 50 | 2-MeO.$C_6H_4$ | 2-bicyclo[2,2,1]heptyl | fumarate | 130–131 |
| 51 | 2-MeNHC(O).$C_6H_4$ | $^tBu$ | fumarate | 134–135.5 |
| 52 | 3-MeNHC(O).$C_6H_4$ | $CH_2{}^tBu$ | hemifumarate | 145–146 |
| 53 | 2-MeO.$C_6H_4$ | $CH(Et)_2$ | hemifumarate | 134–135 |
| 54 | 2-MeO.$C_6H_4$ | $C(Et)Me_2$ | fumarate (0.75) | 115–116 |
| 55 | 3-MeO.$C_6H_4$ | $^tBu$ | fumarate | 148.5–149 |
| 56 | 2-MeO.$C_6H_4$ | 4-methylcyclohexyl | fumarate (0.75) | 127–128 |
| 57 | 3-EtO$_2$CNH.$C_6H_3$ | $C_6H_5$ | oxalate | 175–177 |
| 58 | 2-MeNHC(O).$C_6H_4$ | 4-F.$C_6H_4$ | hemifumarate | 154.5–156 |
| 59 | 2-MeO.$C_6H_4$ | $CH_2$ cyclopentyl | fumarate | 118–119 |
| 60 | 3-H$_2$NC(O)NH.$C_6H_4$ | $C_6H_5$ | oxalate | 141–143 |
| 61 | 2-MeNHC(O).$C_6H_4$ | cyclohexyl | oxalate | 180–182 |
| 62 | 3-MeNHC(O).$C_6H_4$ | cyclohexyl | oxalate | 171–173 |
| 63 | 3-MeC(O)NH.$C_6H_4$ | $CH_2{}^tBu$ | hemifumarate | 166–167 |
| 64 | 2-EtO.$C_6H_4$ | $^tBu$ | fumarate | 131.5–133 |
| 65 | 3-HONC(O).$C_6H_4$ | cyclohexyl | hydrochlorate | 179–180 |
| 66 | 3-EtO$_2$CNH.$C_6H_4$ | cyclohexyl | hydrochlorate | 204.5–205 |
| 67 | 2-MeO$_2$C.$C_6H_4$ | $CH_2{}^tBu$ | hydrochlorate | 157–158 |
| 68 | 3-H$_2$NC(O)NH.$C_6H_4$ | $CH_2{}^tBu$ | hydrochlorate | 144–146 |
| 69 | 2-MeO.$C_6H_4$ | cyclopropyl | fumarate | 90–92 |

By using the procedure indicated above one may likewise prepare the following products which are likewise a part of the invention and which constitute preferred products:

| Compound | Ar | R |
|---|---|---|
| A | 2-HONHC(O).$C_6H_4$ | 4-F.$C_6H_4$ |
| B | 2-HONHC(O).$C_6H_4$ | cycloheptyl |
| C | 2-HONHC(O).$C_6H_4$ | cyclopentyl |
| D | 2-HONHC(O).$C_6H_4$ | cyclopentyl $CH_2$ |
| E | 2-HONHC(O).$C_6H_4$ | adamantyl |
| F | 2-HONHC(O).$C_6H_4$ | $^t$butyl |
| G | 2-HONHC(O).$C_6H_4$ | $^t$butyl $CH_2$ |
| H | 2-MeNHC(O).$C_6H_4$ | cycloheptyl |
| I | 2-MeNHC(O).$C_6H_4$ | cyclopentyl |
| J | 2-MeNHC(O).$C_6H_4$ | cyclopentyl $CH_2$ |
| K | 2-MeNHC(O).$C_6H_4$ | adamantyl |
| L | 2-HO.$C_6H_4$ | 4-F.$C_6H_4$ |
| M | 2-HO.$C_6H_4$ | cycloheptyl |
| N | 2-HO.$C_6H_4$ | cyclohexyl |
| O | 2-HO.$C_6H_4$ | cyclopentyl |
| P | 2-HO.$C_6H_4$ | cyclopentyl $CH_2$ |
| Q | 2-HO.$C_6H_4$ | adamantyl |
| R | 2-HO.$C_6H_4$ | $^t$butyl |
| S | 2-HO.$C_6H_4$ | $^t$butyl $CH_2$ |
| T | 3-H$_2$NC(O)NH.$C_6H_4$ | 4-F.$C_6H_4$ |
| U | 3-H$_2$NC(O)NH.$C_6H_4$ | cycloheptyl |
| V | 3-H$_2$NC(O)NH.$C_6H_4$ | cyclohexyl |
| W | 3-H$_2$NC(O)NH.$C_6H_4$ | cyclopentyl |
| X | 3-H$_2$NC(O)NH.$C_6H_4$ | cyclopentyl $CH_2$ |
| Y | 3-H$_2$NC(O)NH.$C_6H_4$ | adamantyl |
| Z | 3-H$_2$NC(O)NH.$C_6H_4$ | $^t$butyl |
| AA | 3-EtO$_2$CNH.$C_6H_4$ | 4-F.$C_6H_4$ |
| AB | 3-EtO$_2$CNH.$C_6H_4$ | cycloheptyl |
| AC | 3-EtO$_2$CNH.$C_6H_4$ | cyclopentyl |
| AD | 3-EtO$_2$CNH.$C_6H_4$ | cyclopentyl $CH_2$ |
| AE | 3-EtO$_2$CNH.$C_6H_4$ | adamantyl |
| AF | 3-EtO$_2$CNH.$C_6H_4$ | $^t$butyl |
| AG | 3-EtO$_2$CNH.$C_6H_4$ | $^t$butyl $CH_2$ |
| AH | 3-MeO$_2$CNH.$C_6H_4$ | 4-F.$C_6H_4$ |
| AI | 3-MeO$_2$CNH.$C_6H_4$ | $C_6H_5$ |
| AK | 3-MeO$_2$CNH.$C_6H_4$ | cyclohexyl |
| AL | 3-MeO$_2$CNH.$C_6H_4$ | cyclopentyl |
| AM | 3-MeO$_2$CNH.$C_6H_4$ | cyclopentyl $CH_2$ |
| AN | 3-MeO$_2$CNH.$C_6H_4$ | adamantyl |
| AO | 3-MeO$_2$CNH.$C_6H_4$ | $^t$butyl |
| AP | 3-MeC(O)NH.$C_6H_4$ | 4-F.$C_6H_4$ |
| AQ | 3-MeC(O)NH.$C_6H_4$ | $C_6H_5$ |
| AR | 3-MeC(O)NH.$C_6H_4$ | cycloheptyl |
| AS | 3-MeC(O)NH.$C_6H_4$ | cyclohexyl |
| AT | 3-MeC(O)NH.$C_6H_4$ | cyclopentyl |
| AU | 3-MeC(O)NH.$C_6H_4$ | cyclopentyl $CH_2$ |
| AV | 3-MeC(O)NH.$C_6H_4$ | adamantyl |
| AW | 3-MeNHC(O).$C_6H_4$ | 4-F.$C_6H_4$ |
| AX | 3-MeNHC(O).$C_6H_4$ | cycloheptyl |
| AY | 3-MeNHC(O).$C_6H_4$ | cyclopentyl |
| AZ | 3-MeNHC(O).$C_6H_4$ | cyclopentyl $CH_2$ |
| BA | 3-MeNHC(O).$C_6H_4$ | adamantyl |

Pharmacological Study of the Products of the Invention

1) Affinity of the Compounds of the Invention for the 5-HT$_{1A}$ Receptor:

The affinity of the compounds for the 5-HT$_{1A}$ serotonergic receptors is determined by measuring the inhibition of [3H]8-hydroxy-2 (di-n-propylamino) tetralin([3H]8-OH-DPAT) connected with the cerebral cortex of the rat according to the method of Perutka et al. (*J. Neurochem.*, 47,529 [1986]).

Cerebral cortices of male Sprague Dawley rats are homogenized in 50 mM Tris-HCl, pH—7.4, and centrifuged at 40,000 g for 10 min. at 4 degrees C. Pellets are put into suspension in the same buffer and incubated for 10 min. at 37 degrees C. and the homogenates are again centrifuged at 40,000 g for 10 min. at 4 degrees C.

Competitive inhibition tests of the bond of [3H]8-OH-DAPT are performed three times with unmarked competitors with concentrations ranging between 100 pM and 100 µM. Rat cerebral cortex membranes (10 mg by weight, moistened, per ml) are incubated with [3H]8-OH-DPAT (1 nM) for 30 min. at 25 deg. C. in Tris-HCl 50 mM, pH 7.4 comprising 4 mM of CaCl$_2$, 10 µM of pargylin and 0.1% ascorbic acid.

The bonded [3H]8-OH-DPAT is separated from the free [3H]8-OH-DPAT by immediate filtration by means of Whatman GF/B fiberglass filters using a Brandel cell recoverer. The filters [filtrates?] are washed three times with the same buffer at 0–4 deg. C. and their radioactivity is determined by means of a liquid scintillation spectrometer.

The specific bond is obtained by subtracting the given bond in the presence of 1 $\mu$M of 8-OH-DPAT from the total bond. The bond characteristics are analyzed by interactive analysis of the nonlinear regression by computer using the Ligand program (Munson and Rodbard, *Anal. Biochem.*, 107, 220 [1980]).

The result for representative compounds of the invention are given in Table 2. Buspirone, the 5-HT$_{1A}$ counteracting agent used clinically is cited as a reference.

TABLE 2

| Compound No. | Ki (nM) |
|---|---|
| 1 | 0.20 |
| 2 | 0.10 |
| 3 | 1.4 |
| 11 | 0.71 |
| 14 | 1.6 |
| 20 | 0.23 |
| 23 | 0.33 |
| 30 | 0.44 |
| 33 | 0.33 |
| 34 | 0.087 |
| 45 | 0.14 |
| 46 | 0.094 |
| 50 | 0.071 |
| 59 | 0.65 |
| 64 | 0.77 |
| Buspirone | 20 |

2) Gastric Anti-secretion Activity

The gastric anti-secretion activity of the compounds of the invention was tested according to the method described by Shay et al. (H. Shay, D. C. Sun, M. Gruenstein, *Gastroenterology*, 26, 906 [1954]). Thus, male Sprague Dawley rats weighing around 200 g with free access to water are made to fast 24 hours before the experiments. Ligatures are made on the pylora under ether anesthesia and the medications to be tested are simultaneously administered either by the intraperitoneal route (i.p.) or by intraduodenal route (i.d.). The abdomen is closed again and the animals are sacrificed after four hours. The gastric secretion is recovered and centrifuged at 1,500 g for 15 minutes; the volume of the supernatant is measured and the acidity is determined by automatic titration of 0.05 N sodium hydroxide. A control group is included for each experiment.

The dose necessery for 50% inhibition (ED$_{50}$) of the acid secretion (X concentration of hydrochloric acid by volume) is calculated using the method described by Litchfield and Wilcoxon (J. T. Litchfield, F. A. Wilcoxon, *J. Pharmacol.*, 96, 99 [1949]). The results obtained for compounds representative of the invention are given in Table 3 and compared with the clinically used reference compounds: Pirenzepine (anti-cholinergic), Ranitidine (antagonist of histaminergic H$_2$ receptors) and Omeprazole (proton pump inhibitor).

TABLE 3

| Compound No. | ED$_{50}$ (mg/kg i.d.) |
|---|---|
| 1 | 3.7 |
| 2 | 3.6 |
| 18 | 3.2 |
| 20 | 3.1 |
| Pirenzepine | 14 |

TABLE 3-continued

| Compound No. | ED$_{50}$ (mg/kg i.d.) |
|---|---|
| Ranitidine | 22 |
| Omeprazole | 4.6 |

3) Anti-emetic Activity of the Compounds of the Invention—Inhibition of Vomiting Induced by cis-Platinum:

Inhibition induced by cis-platinum is evaluated in ferrets using a modification of the protocol described by Barnes et al. (J. M. Barnes, N. M. Barnes, B. Costall, R. J. Naylor, F. D. Tattersall, *Neuropharmacology*, 27[8], 783 [1988]). Thus, albino ferrets or European polecats of both sexes weighing between 0.5 kg and 1.5 kg are put under anesthesia with pentobarbitone (30–40 mg/kg i.p.) and a polyethylene injection tube is inserted into the left jugular vein. Two days later, the compounds being tested are administered i.v. 30 minutes before cis-platinum (30 mg/kg i.v.). The animals are observed for six hours and the number of vomitings is recorded. A control group is included for each experiment.

The results of the compounds representative of the invention are given in Table 4 and compared with the clinically used reference compounds Ondansetron (5-HT$_3$ antagonist) and Metoclopramide (D$_2$ antagonist).

TABLE 4

| Compound No. | Dose (mg/kg iv) | Percent Inhibition |
|---|---|---|
| 1 | 1.0 | 40 |
| 18 | 1.0 | 62 |
| Ondansetron | 0.5 | 62 |
| Metoclopramide | 1 | 15 |

4) Effect of the Products of the Invention on Intestinal Transit:

A compound of the invention was tested to determine its effect on the intestinal transit according to the method described by A. F. Green (*Br. J. Pharmacol.*, 14, 26–34 [1959]). To male Sprague Dawley rats weighing approximately 200 g before being made to fast, there was administered (p.o.) a meal comprised of charcoal (10 g) and gum arabic (2.5 g) dissolved in 100 ml of distilled water. The animals were sacrificed after 15 minutes and the charcoal transit time was measured.

The product to be tested was administered (s.c.) 30 minutes before the administration of the charcoal. The results obtained with compound No. 18 are listed in Table 5.

TABLE 5

| Compound No. | Dose (mg/kg s.c.) | Charcoal Transit Time Compared to Control |
|---|---|---|
| 18 | 0.3 | +16% |
|  | 1.0 | +20% |

5) Effects of the Products of the Invention on Gastric Emptying:

A compound of the invention was tested for its effect on gastric emptying according to the method described by C. Scarpignato et al. (*Arch. Int. Pharmacodyn.*, 246, 286–294 [1980]). Thus, 1.5 ml of a 1.5% methyl cellulose solution comprising phenol red (0.5 mg/ml) was administered orally to Sprague Dawley rats weighing approximately 200 g and previously subjected to fasting. The animals were sacrificed after 15 minutes and the pylora and the esophagi were tied off. The contents of the stomachs were collected in a teflon beaker containing a solution of soda (100 ml at 0.1 N) and the mixture was homogenized. The proteins were precipitated by addition of 0.5 ml of a 20% aqueous solution of trifluoroacetic acid to a 5 ml portion of homogenate. After centrifuging, the part of the solution rising to the top was separated and added to 4.5 ml of an aqueous solution of soda at 0.5 N and the phenol red content was determined by using a spectrophotometer at a wavelength of 560 nM.

The compound to be tested was administered (s.c.) 15 minutes with the administration of phenol red.

The result obtained with compound No. 18 are indicated in Table 6.

TABLE 6

| Compound No. | Dose (mg/kg s.c.) | Effect on Gastric Emptying Time Compared to Control |
|---|---|---|
| 18 | 0.3 | +8% |
|  | 1.0 | +18% |
|  | 3.0 | +26% |

What is claimed is:

1. A compound selected from the group consisting of a compound of the formula

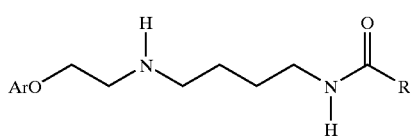

I wherein Ar is unsubstituted or substituted phenyl with at least one member selected from the group consisting of halogen, alkyl and alkoxy of 1 to 6 carbon atoms, —CN, —NO$_2$, —OH,

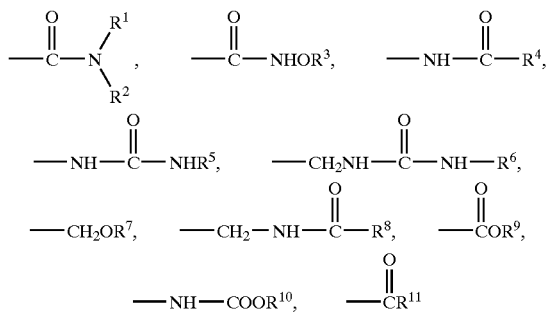

and —SR$^{12}$, R$^1$, R$^2$, R$^3$, R$^4$, R$^5$, R$^6$, R$^7$ and R$^8$ are independently hydrogen or lower alkyl and R$^9$, R$^{10}$, R$^{11}$ and R$^{12}$ are independently lower alkyl and R is selected from the group consisting of alkyl, alkenyl and alkynyl of up to 10 carbon atoms, phenyl unsubstituted or substituted with at least one member of the group consisting of alkyl and alkoxy of 1 to 6 carbon atoms, halogen, —OH, —NO$_2$, —NH$_2$ and acylamino of an organic carboxylic acid and cycloalkyl, alkylcycloalkyl and cycloalkylalkyl of up to 7 carbon atoms and their non-toxic, pharmaceutically acceptable acid addition salts.

2. A compound of claim 1 wherein Ar is phenyl substituted with at least one member of the group consisting of —OH, methoxy,

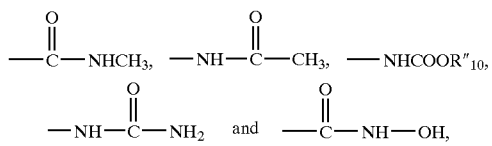

R"$_{10}$ is methyl or ethyl and R is selected from the group consisting of cyclopentyl, cyclohexyl, cycloheptyl, cyclopentylmethyl, tertiary butyl, neopentyl, phenyl, adamantyl and fluorophenyl.

3. A compound of claim 1 selected from the group consisting of:

N[4-{2-(2-methoxyphenoxy)ethyl}aminobutyl] benzamide;

N[4-{2-(2-methoxyphenoxy)ethyl}aminobutyl] adamantamide;

N[4-{2-(2-methylamino carbonyl phenoxy)ethyl] amino}butyl]benzamide;

N[4-{2-(2-hydroxyphenoxy)ethyl}aminobutyl] benzamide;

N[4-{2-(2-methoxyphenoxy)ethyl}aminobutyl] cyclohexylamide;

N[4-{2-(2-methoxyphenoxy)ethyl}aminobutyl] cycloheptylamide;

N[4-{2-(2-methoxyphenoxy)ethyl}aminobutyl]2-bicyclo [2,2,1]heptylamide.

4. A composition for inhibiting gastric acid secretion comprising an amount of a compound of claim 1 sufficient to inhibit gastric acid secretion and an inert pharmaceutical carrier.

5. A composition for treating cardiovascular diseases comprising an effect amount of a compound of claim 1 to treat cardiovascular diseases and an inert pharmaceutical carrier.

6. The composition of claim 5 wherein the cardiovascular disease is hypertension.

7. A method of treating hypertension in warm-blooded animals in need thereof comprising administering to warm-blooded animals a hypertensively effective amount of a compound of claim 1.

8. A method inhibiting gastric acid secretion in warm-blooded animals comprising administering to warm-blooded animals an amount of a compound of claim 1 sufficient to inhibit gastric acid secretion.

9. A method of treating anxiety, depression or sleep disorders in warm-blooded animal comprising administering to warm-blooded animals an amount of a compound of claim 1 sufficient to inhibit anxiety, depression and sleep disorders.

10. A process for the preparation of a compound of claim 1 comprising reacting a compound of the formula

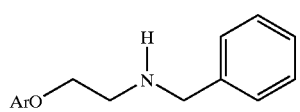

II wherein Ar is as defined in claim 1 with a compound of the formula

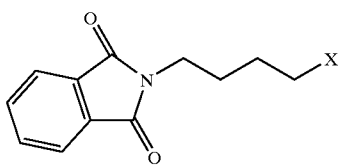
III wherein X is halogen or psuedo halogen to obtain a compound of the formula

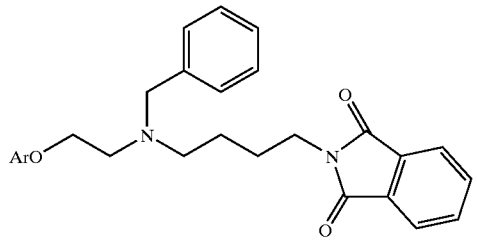
IV reacting the latter to remove the phthalimido group to obtain a compound of the formula

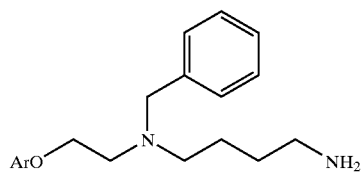
V and reacting the latter with an acylating agent of RCOOH wherein R is defined as in claim 1 to obtain a compound of the formula

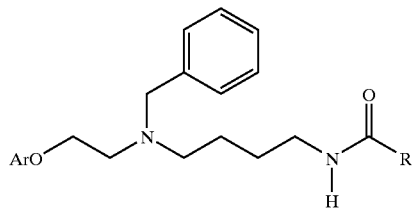
VI

11. A process for the preparation of a compound of claim 1 comprising reacting a compound of the formula

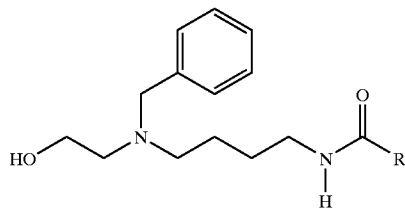
VII with N-benzylethanolamine to obtain a compound of the formula

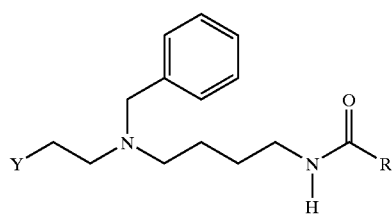
VIII reacting the latter with a halogenating agent to obtain a compound of the formula

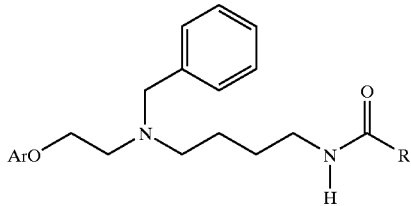
IX wherein Y is halogen, reacting the latter with ArOH wherein Ar is defined as in claim 1 to obtain a compound of the formula

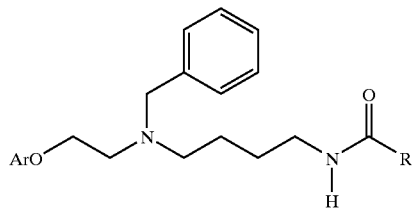
VI and removing the benzyl group.

* * * * *

UNITED STATES PATENT AND TRADEMARK OFFICE
CERTIFICATE OF CORRECTION

PATENT NO.      : 6,670,400 B1
DATED           : December 30, 2003
INVENTOR(S)     : Dennis Bigg et al.

It is certified that error appears in the above-identified patent and that said Letters Patent is hereby corrected as shown below:

<u>Title page,</u>
Item [75], Inventors, please correct the spelling of the widow to read -- Christiane Charlotte Paule Defaux --

Signed and Sealed this

First Day of June, 2004

JON W. DUDAS
*Acting Director of the United States Patent and Trademark Office*